(12) United States Patent
Wand

(10) Patent No.: US 7,468,198 B2
(45) Date of Patent: Dec. 23, 2008

(54) LIQUID CRYSTAL COMPOUND, FERROELECTRIC LIQUID CRYSTAL COMPOSITION, AND FERROELECTRIC LIQUID CRYSTAL DISPLAY

(75) Inventor: Michael Wand, Boulder, CO (US)

(73) Assignee: Dai Nippon Printing Co. Ltd., Tokyo-to (JP)

( * ) Notice: Subject to any disclaimer, the term of this patent is extended or adjusted under 35 U.S.C. 154(b) by 98 days.

(21) Appl. No.: 11/690,277

(22) Filed: Mar. 23, 2007

(65) Prior Publication Data

US 2008/0230745 A1    Sep. 25, 2008

(51) Int. Cl.
  *C09K 19/34* (2006.01)
  *C07D 403/10* (2006.01)
  *C07D 333/04* (2006.01)

(52) U.S. Cl. ............... 428/1.3; 252/299.61; 544/310; 549/4; 549/59; 549/66

(58) Field of Classification Search ............ 252/299.61; 428/1.3; 544/310; 549/4, 59, 66
See application file for complete search history.

(56) References Cited

U.S. PATENT DOCUMENTS

| | | | | |
|---|---|---|---|---|
| 5,116,530 A | * | 5/1992 | Togano et al. | 252/299.61 |
| 5,250,218 A | * | 10/1993 | Mori et al. | 252/299.61 |
| 5,395,551 A | * | 3/1995 | Togano et al. | 252/299.61 |
| 5,413,735 A | * | 5/1995 | Yamashita et al. | 252/299.61 |

OTHER PUBLICATIONS

Nonaka, T., et al., "Material characteristics of an active matrix LCD based upon chiral smectics." 1999. *Liquid Crystals*, vol. 26, No. 11, pp. 1599-1602.

* cited by examiner

*Primary Examiner*—Shean C Wu
(74) *Attorney, Agent, or Firm*—Ladas & Parry LLP

(57) ABSTRACT

A liquid crystal compound represented by the following formula is provided to enhance the contrast of a liquid crystal device using ferroeloctric liquid crystal:

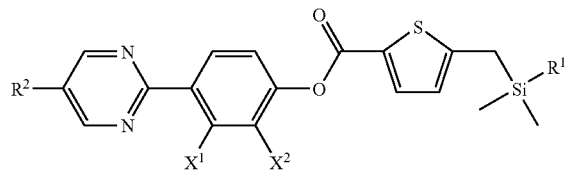

$R^1$ is an alkyl group having 4 to 6 carbon atoms. $R^2$ is an alkyl group having 6 to 18 carbon atoms or an alkoxy group having 6 to 18 carbon atoms. $X^1$ and $X^2$ are each independently hydrogen ox fluorine.

4 Claims, 4 Drawing Sheets

LIQUID CRYSTAL COMPOUND, FERROELECTRIC LIQUID CRYSTAL COMPOSITION, AND FERROELECTRIC LIQUID CRYSTAL DISPLAY

BACKGROUND OF THE INVENTION

1. Field of the Invention

The present invention relates generally to a liquid crystal compound, and more particularly to a liquid crystal compound used for producing a liquid crystal device using ferroelectric liquid crystal, and a ferroelectric liquid crystal composition, and a ferroelectric liquid crystal device using the liquid crystal compound.

2. Description of the Related Art

The sharp rise in demand for personal computers, especially the portable computers, has fueled the ever-increasing demand for liquid crystal displays in recent years. Liquid crystal televisions for home use are also gaining popularity, and as such the market for liquid crystal displays is continually expanding. The liquid crystal displays are now widely available in larger screen sizes, particularly in the case of the liquid crystal televisions for home use. In view of these trends, researches are in progress to further improve quality and to impart new functions to the liquid crystal displays.

Currently, the dominant design for liquid crystal displays includes: a TFT electrode substrate having TFT electrodes and pixel electrodes; a color filter substrate having a color filter layer to achieve color display; and a liquid crystal material is usually encapsulated between the TFT electrode substrate and the color filter substrate. These liquid crystal displays operate in various driving modes (such as TN, STN, MVA, IPS, and OCB) classified by the orientation of the liquid crystal material, of which TN, STN, and MVA mode liquid crystal displays are more widely used.

However, in the case of the liquid crystal displays as described above, the response speed of the liquid crystal materials is considered to be generally slow as it can be anywhere from several milliseconds to several tens of milliseconds. The slow response speed of the conventional liquid crystal displays speed leads to inferior performance of displaying moving images as compared to the conventional CRT displays or the PDPs that are also gaining popularity.

To increase the response speed in a liquid crystal display device, ferroelectric liquid crystal is gaining attention for its ability to provide the high response speed on the order of µs, which is much faster than that of the liquid crystal materials described above. It is expected that the liquid crystal displays utilizing the high response speed of the ferroelectric liquid crystal materials will one day be displaying moving images in a level of quality equal to that of the CRT displays or the PDPs.

The ferroelectric liquid crystal of a bistable liquid crystal has been known. A bistable liquid crystal has two stable states to show bistability when no voltage is applied, but a bistable liquid crystal cannot attain the graduation display. However, the ferroelectric liquid crystal in which the liquid crystal layer is stable in a single state (i.e., "monostable") when no voltage is applied is gaining attention, as the monostable liquid crystal can provide graduation display by continuously changing the director (i.e., the inclination of the molecule axis) of the liquid crystal with a change in applied voltage (NONAKA, T., L I, J., OGAWA, A., HORNUNG, B., SCHMIDT, W., WINGEN, R., and DUBAL, H., 1999, Liq. Cryst., 26, 1599., also see FIG. 4). Some known monostable liquid crystal materials are:

(1) a ferroelectric liquid crystal in which phase change is caused in temperature lowering process between cholestric phase (Ch) and chiral smectic C phase (SmC*) via no smectic A phase (SmA); and (2) a ferroelectric liquid crystal in which phase change is caused in temperature lowering process as Ch-SmA-SmC* and shows SmC* phase via SmA phase (see FIG. 5).

Therefore, the monostable ferroelectric liquid crystals made possible to obtain liquid crystal displays with faster moving images display characterstics.

Not only the above-described ability to ably display moving images, various other display quality characteristics, such as contrast, luminance and chromaticity characteristics, are also required in the modern liquid crystal displays. Some of these display quality characteristics sought to be enhanced vary depending on the driving mode of the liquid crystal display, but for enhancing contrast liquid crystal displays are required to use ferroelectric liquid crystals.

The liquid crystal display contrast depends on the degree of change in the alignment state of a liquid crystal material caused by application of voltage. Therefore, the contrast of liquid crystal displays using the ferroelectric liquid crystals could be enhanced mainly by adjusting the composition of the liquid crystal materials. More specifically, the liquid crystal displays using ferroelectric liquid crystals usually use a liquid crystal composition containing plural kinds of liquid crystal compounds, and therefore enhancement of the contrast of the ferroelectric liquid crystal displays is achieved by replacing one or more kinds of the liquid crystal compounds contained in the liquid crystal composition with other different kinds of liquid crystal compounds or by changing the composition ratio of liquid crystal compounds constituting the liquid crystal composition.

However, the conventional liquid crystal compounds have problems in that it is difficult to achieve desired contrast by changing the composition ratio of liquid crystal compounds or by selecting the kinds of liquid crystal compounds contained in a liquid crystal composition. In order to solve these and other problems, there is a need for providing liquid crystal compounds capable of drastically enhancing the contrast of a liquid crystal display using ferroelectric liquid crystal.

SUMMARY OF THE INVENTION

In view of the above problem, the present invention provides a liquid crystal compound that can enhance the contrast of a liquid crystal device using ferroelectric liquid crystal.

To solve the above-mentioned problems, the present invention provides a liquid crystal compound having a structure represented by the following formula (I):

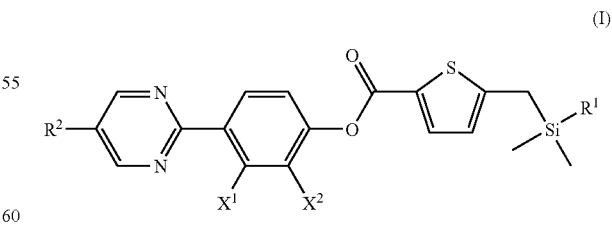

where $R^1$ is an alkyl group having 4 to 6 carbon atoms, $R^2$ is an alkyl group having 6 to 18 carbon atoms or an alkoxy group having 6 to 18 carbon atoms, and $X^1$ and $X^2$ are each independently hydrogen or fluorine.

When the liquid crystal compound of the present invention having a structure represented by the above formula (I) is used together with ferroelectric liquid crystal for producing a liquid crystal device using ferroelectric liquid crystal, a liquid crystal device having excellent contrast characteristics can be obtained.

The liquid crystal compound of the present invention is preferably used as a contrast enhancer for enhancing the contrast of a ferroelectric liquid crystal device using a ferroelectric liquid crystal. This is because among various advantageous effects that the liquid crystal compound according to an embodiment of the present invention having a structure represented by the above formula (I) can exert on a ferroelectric liquid crystal device using ferroelectric liquid crystal, the contrast-enhancing effect of the liquid crystal compound is especially excellent.

The present invention further provides a ferroelectric liquid crystal composition comprising the above-mentioned liquid crystal compound and a ferroelectric liquid crystal.

When the ferroelectric liquid crystal composition of the present invention containing the liquid crystal compound according to the present invention is used for producing a liquid crystal device, a ferroelectric liquid crystal device having excellent contrast characteristics can be obtained.

The present invention also provides a ferroelectric liquid crystal device comprising: a first liquid crystal display substrate having a first substrate, a first electrode formed on the first substrate, and a first alignment layer formed on the first electrode and exerting alignment-regulating force on a ferroelectric liquid crystal; a second liquid crystal display substrate having a second substrate, a second electrode formed on the second substrate, and a second alignment layer formed on the second electrode and exerting alignment-regulating force on the ferroelectric liquid crystal; and a liquid crystal layer, containing a ferroelectric liquid crystal, interposed between the first liquid crystal display substrate and the second liquid crystal display substrate, which are arranged such that the first alignment layer and the second alignment layer are opposed to each other, wherein the liquid crystal layer contains the above-mentioned liquid crystal compound.

In the present invention, a ferroelectric liquid crystal device having excellent contrast characteristics can be obtained by the liquid crystal layer containing the liquid crystal compound.

When used for producing a liquid crystal device using ferroelectric liquid crystal, the liquid crystal compound of the present invention has the effect of enhancing the contrast characteristics thereof.

These and various other features as well as advantages which characterize the present invention will be apparent from a reading of the following detailed description of specific embodiments and a review of the associated drawings.

DESCRIPTION OF THE PREFERRED EMBODIMENTS

Figure 1:
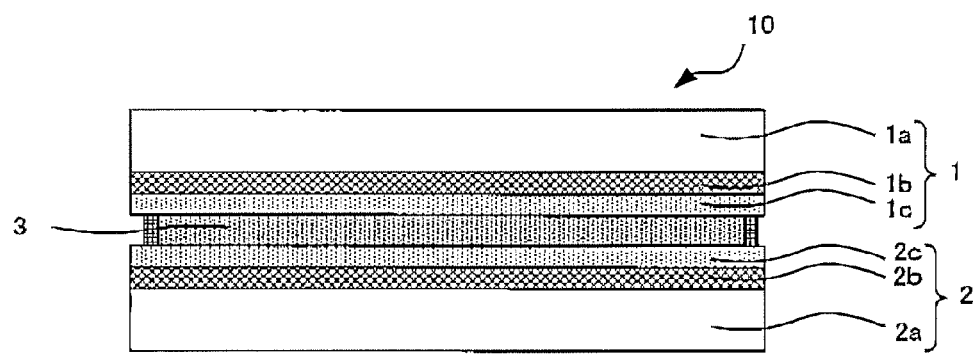
FIG. 1 is a schematic view showing one example of a ferroelectric liquid crystal device according to an embodiment of the present invention.

The present invention relates to a liquid crystal compound, and a ferroelectric liquid crystal composition and ferroelectric liquid crystal device using the liquid crystal compound.

Hereinafter, the liquid crystal compound, the ferroelectric liquid crystal composition, and the ferroelectric liquid crystal device according to various embodiments of the present invention will be explained in turn.

A. Liquid Crystal Compound

The liquid crystal compound according to an embodiment of the present invention has a structure represented by the following formula (I).

$$\text{(I)}$$

When the liquid crystal compound having the structure represented by the above formula (I) is used together with the ferroelectric liquid crystals for producing a liquid crystal device, excellent contrast characteristics are achieved in the liquid crystal display devices using the ferroelectric liquid crystals.

Further, when a mixture of plural kinds of the liquid crystal compounds that are different in the number of carbons of $R^1$ or $R^2$ in the above formula (I) is used for producing a liquid crystal device according to an embodiment of the present invention, there is also an advantage that a liquid crystal device having a wide driving temperature margin can be obtained.

If necessary, a liquid crystal compound may contain fluorine as $X^1$ or $X^2$ in the above formula (I) according to an embodiment of the present invention. When such a liquid crystal compound is used for producing a liquid crystal device, a liquid crystal device having a high response speed can be obtained.

As described above, the liquid crystal compound of the present invention enhances the contrast of a liquid crystal device using ferroelectric liquid crystal Hereinafter, the liquid crystal compound according to an embodiment of the present invention will be described in detail.

(1) Liquid Crystal Compound

The liquid crystal compound of the present invention is characterized by having a structure represented by the above formula (I). The liquid crystal compound of the present invention is not particularly limited but includes any and all structures that can be represented by the formula (I) Therefore, $R^1$, $R^2$, $X^1$, and $X^2$ in the formula (I) can be appropriately determined in accordance with the intended use of the liquid crystal compound.

According to an embodiment of the present invention, $R^1$ in the formula (I) represents an alkyl group having 4 to 6 carbon atoms. The alkyl group may be either a linear alkyl group lacking a branched chain or a branched alkyl group having a branched chain. In addition, the alkyl group may be either a saturated alkyl group whose carbon-carbon bonds are all saturated bonds or an unsaturated alkyl group having a carbon double bond or a carbon triple bond. In addition, the alkyl group may contain any optional functional group.

$R^2$ in the formula (I) represents an alkyl group having 6 to 18 carbon atoms or an alkoxy group having 6 to 18 carbon atoms. As in the case of $R^1$, the alkyl group represented by $R^2$ (in a case where $R^2$ is an alkoxy group, a hydrocarbon chain portion) may be either a linear alkyl group, lacking a branched chain, or a branched alkyl group having a branched chain. In addition, the alkyl group may be either a saturated alkyl group whose carbon-carbon bonds are all saturated bonds or an unsaturated alkyl group having a carbon double bond or a carbon triple bond. In addition, the alkyl group may contain any optional functional group.

$X^1$ and $X^2$ in the formula (I) could represent any combination of hydrogen and/or fluorine. That is, according to an embodiment of the present invention, both $X^1$ and $X^2$ may be fluorine or hydrogen, or one of $X^1$ and $X^2$ maybe fluorine while the other is hydrogen. When at least one of $X^1$ and $X^2$ is fluorine in the liquid crystal compound used for producing a liquid crystal device using ferroelectric liquid crystal, there is an advantage that a ferroelectric liquid crystal device having a high response speed can be obtained.

Specific examples of such a liquid crystal compound according to an embodiment of the present invention include the compounds represented by the following formulas:

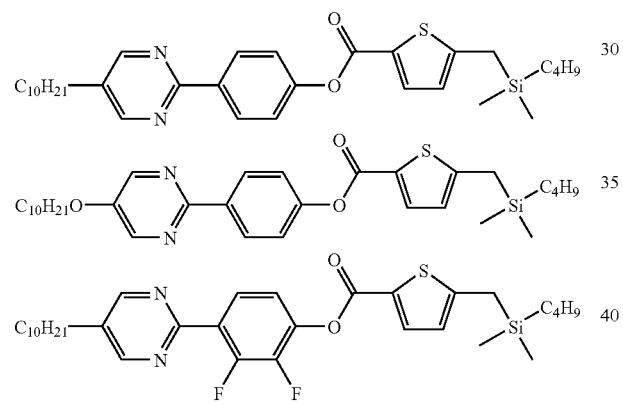

When used for producing a liquid crystal device, these liquid crystal compounds having a structure represented by the formula (I) can exert various advantageous effects such as enhancement of contrast characteristics and increase in the response speed. Among them, a compound represented by, for example, the following formula provides particularly excellent contrast-enhancing effects.

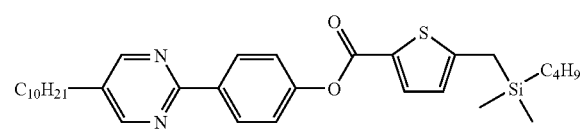

Accordingly, the liquid crystal compounds represented by the formula (I) are very effective contrast enhancer for enhancing the contrast of a ferroelectric liquid crystal device using ferroelectric liquid crystal.

(2) Method of Synthesizing Liquid Crystal Compound

The liquid crystal compound of the present invention can be synthesized by an organic synthesis method using some optional compounds as raw materials. Hereinafter, the following flow chart will be described as one example of a method of synthesizing a liquid crystal compound according to an embodiment of the present invention.

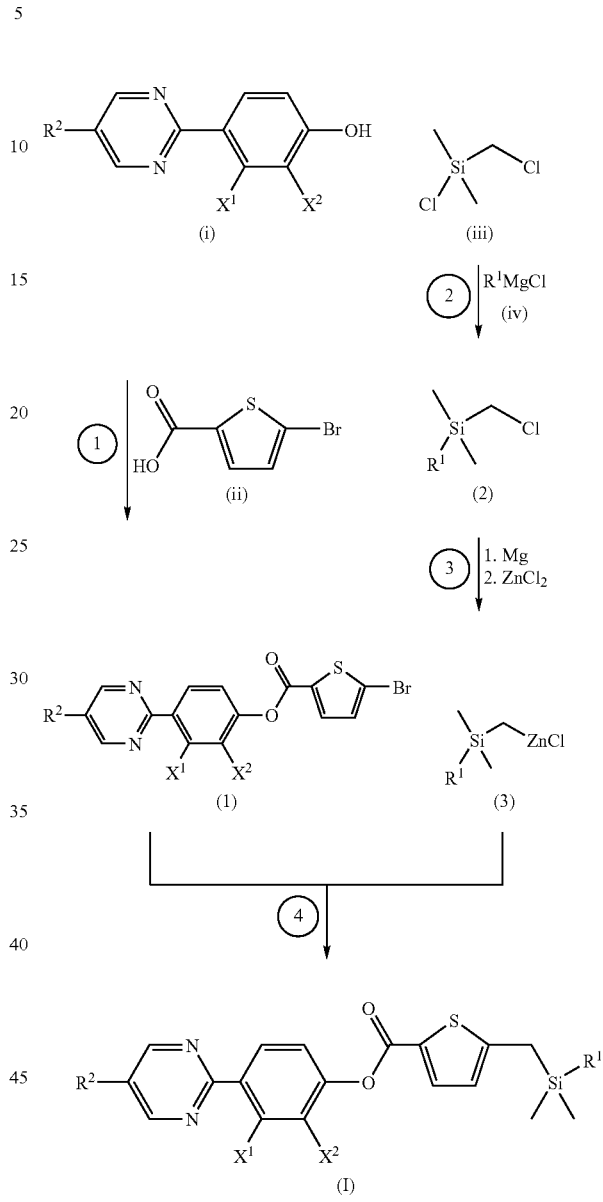

This synthesis method includes a first step of synthesizing a compound (1), a second step of synthesizing a compound (2), a third step of synthesizing a compound (3) from the compound (2), and a fourth step of synthesizing a liquid crystal compound (I) from the compound (1) and the compound (3) These steps will be described in order.

In the first step, a compound (i) and a compound (ii) are subjected to an ester condensation reaction to synthesize a compound (1). By using a compound (i) having the given $R^2$, $X^1$, and $X^2$ as a raw material, an obtained liquid crystal compound represented by the formula (I) can have an alkyl group or alkoxy group with a desired number of carbon atoms as $R^2$ and hydrogen and/or fluorine as $X^1$ and $X^2$. Specific examples of the compound (i) to be used in the first step include compounds represented by the following formulas:

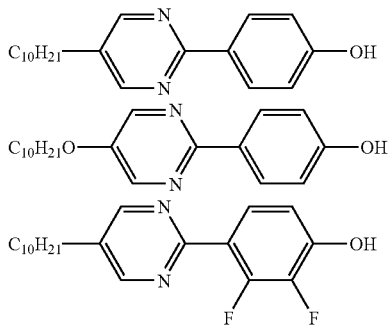

In the second step, a compound (iii) is reacted with a compound (iv) to synthesize a compound (2). By using a compound (iv) having the given $R^1$ as a raw material, an obtained liquid crystal compound represented by the formula (I) can have an alkyl group with a desired number of carbons as $R^1$. A specific example of the compound (iv) to be used in the second step includes $C_4H_9MgCl$.

In the third step, the compound (2) produced in the second step is reacted with Mg and $ZnCl_2$ to synthesize a compound (3).

In the fourth step, the compound (1) produced in the first step is reacted with the compound (3) produced in the third step to obtain a liquid crystal compound (I) according to an embodiment of the present invention. It is to be noted that the reaction between the compound (1) and the compound (3) in the fourth step for obtaining a liquid crystal compound (I) is usually carried out in the presence of a catalyst such as LiBr or Pd.

According to such a synthesis method, by appropriately selecting a combination of the compound (i) and the compound (iv), it is possible to synthesize a given compound having a structure represented by the formula (I).

(3) Intended Use of Liquid Crystal Compound

The intended use of the liquid crystal compound of the present invention is not particularly limited, but the liquid crystal compound according to an embodiment of the present invention is preferably used as a contrast enhancer for enhancing the contrast of a liquid crystal device using ferroelectric liquid crystal. Such a liquid crystal device using ferroelectric liquid crystal usually has a structure in which a liquid crystal layer containing a ferroelectric liquid crystal is interposed between two substrates each having an alignment layer and an electrode. It is most preferred that the liquid crystal compound according to an embodiment of the present invention is contained in the liquid crystal layer to be used together with ferroelectric liquid crystal, thereby enabling a liquid crystal device having excellent contrast characteristics to be obtained.

In the case where the liquid crystal compound according to an embodiment of the present invention is used for producing such a liquid crystal device using ferroelectric liquid crystal, a mixture of the liquid crystal compounds is preferably used. This is because the use of a mixture of the liquid crystal compounds for producing a liquid crystal device may contribute to enhancement of other characteristics associated with display quality of the liquid crystal device. For example, by using a mixture of plural kinds of the liquid crystal compounds of the present invention different in the number of carbon atoms of each of the alkyl groups represented by $R^1$ and $R^2$ in the formula (I), it is possible to prevent the crystallization of the liquid crystal compounds over a wide range of temperatures, thereby enabling a liquid crystal device having a wide driving temperature margin to be obtained.

B. Ferroelectric Liquid Crystal Composition

The ferroelectric liquid crystal composition according to an embodiment of the present invention is characterized by containing the liquid crystal compound of the present invention and a ferroelectric liquid crystal More specifically, the ferroelectric liquid crystal composition according to an embodiment of the present invention is characterized by containing a liquid crystal compound having a structure represented by the formula (I) and a ferroelectric liquid crystal.

When the ferroelectric liquid crystal composition according to an embodiment of the present invention containing the liquid crystal compound of the present invention is used for producing a liquid crystal device, a ferroelectric liquid crystal device having excellent contrast characteristics can be obtained.

The ferroelectric liquid crystal composition according to an embodiment of the present invention contains, as essential components, the liquid crystal compound of the present invention as described above and a ferroelectric liquid crystal, and, it necessary, may further contain any other optional component.

Hereinafter, these components of the ferroelectric liquid crystal composition according to an embodiment of the present invention will be described in order.

1. Liquid Crystal Compound

The liquid crystal compound of present invention described above, that is, a liquid crystal compound having a structure represented by the formula (I), is used.

The ferroelectric liquid crystal composition according to an embodiment of the present invention contains only one or two or more kinds of the liquid crystal compounds, but preferably contains two or more kinds of the liquid crystal compounds. This is because the use of two or more kinds of the liquid crystal compounds for producing a liquid crystal device may contribute to enhancement of the other characteristics associated with the display quality of the liquid crystal device. For example, by using a mixture of the liquid crystal compounds different in the number of carbon atoms of each of the alkyl groups represented by $R^1$ and $R^2$ in the formula (I), it is possible to prevent the crystallization of the liquid crystal compounds over a wide range of temperatures, thereby enabling a ferroelectric liquid crystal composition, which can be used for producing a liquid crystal device having a wide driving temperature margin, to be obtained.

It is to be noted that the liquid crystal compound for use in this section is the same liquid crystal compound described above in the section "A. Liquid Crystal Compound", and therefore the description thereof will not be repeated here.

2. Ferroelectric Liquid Crystal

A ferroelectric liquid crystal to be used in any embodiment of the present invention is not particularly limited as long as it has compatibility with the liquid crystal compound of the present invention and as long as it can exhibit a chiral smectic C (SmC*) phase.

The ferroelectric liquid crystal to be used in any embodiment of the present invention can be broadly divided into two types: one is a material having the phase series that changes from a nematic (N) phase through a cholesteric (Ch) phase to a chiral smectic C (SmC*) phase or from a nematic (N) phase to a chiral smectic C (SmC*) phase—that is, a material whose phase series does not have a smectic A (SmA) phase (i.e., the First Embodiment as described below); and the other is a material whose phase series has a smectic A (SmA) phase (i.e., the Second Embodiment as described below).

First Embodiment of Ferroelectric Liquid Crystal

The ferroelectric liquid crystal of the first embodiment is a material, the phase series of which changes as N-Ch- SmC* or N-SmC*, that is, a material, the phase series of which changes via no SmA phase.

When such a ferroelectric liquid crystal of the first embodiment is used for producing a liquid crystal device, there is an advantage in that the obtained liquid crystal device can be driven by an active matrix system using thin film transistors (TFTs), and the gradation of the liquid crystal device can be controlled by modulating voltage. Accordingly, a liquid crystal device using the ferroelectric liquid crystal of the first embodiment can achieve high-precision and high-quality display. In addition, the ferroelectric liquid crystal of the first embodiment can be preferably used for producing a liquid crystal device displayed by a field sequential color system.

As the ferroelectric liquid crystal of the first embodiment, a liquid crystal material having mono-stability is preferably used. As described above, the term "mono-stability" herein means a nature where the liquid crystal has only one stable state when no voltage is applied thereto. Particularly preferable is a ferroelectric liquid crystal undergoing half-V-shaped driving, in which liquid crystal molecules thereof work only when either a positive or negative voltage is applied thereto because such a liquid crystal makes it possible to lengthen the aperture time of a black and white shutter and therefore realize bright color display.

One example of the ferroelectric liquid crystal of the first embodiment includes "R2301" available from AZ Electronic Materials.

Second Embodiment of Ferroelectric Liquid Crystal

The ferroelectric liquid crystal of the second embodiment is a material that exhibits a SmC* phase via a SmA phase in a temperature lowering process and which shows mono-stability in the SmC* phase.

As in the case of the above-described ferroelectric liquid crystal of the first embodiment, a liquid crystal device using such a monostable liquid crystal material as the ferroelectric liquid crystal of the second embodiment can be driven by an active matrix system using thin film transistors (TFTS), and the gradation of the liquid crystal device can be controlled by modulating voltage, thereby realizing high-precision and high-quality display. In addition, the ferroelectric liquid crystal of the second embodiment has an advantage that it can be selected from a wide range of choices.

The ferroelectric liquid crystal of the second embodiment is not particularly limited as long as it shows a SmC* phase via a SmA phase in a temperature lowering process, and it may show another liquid crystal phase on the higher temperature side or the lower temperature side of these liquid crystal phases. Among such materials, a material showing a SmC* phase from a Ch phase via a SmA phase is preferably used because of its wide range of choices. Such a ferroelectric liquid crystal can be selected from various generally known materials according to required characteristics.

As such a ferroelectric liquid crystal, a single material showing a SmC* phase can be used, but a material obtained by adding a small amount of a chiral dopant, not showing a SmC phase by itself but capable of inducing large spontaneous polarization and an appropriate spiral pitch, to a low-viscosity non-chiral liquid crystal easily showing a SmC phase (hereinafter, also referred to as a "host liquid crystal"), so as to show the above-described phase series, is preferably used because it has a low viscosity and can realize faster response.

As such a host liquid crystal, a material showing a SmC phase over a wide range of temperatures is preferred. The host liquid crystal to be used is not particularly limited as long as it is a material generally known as a host liquid crystal for ferroelectric liquid crystal, and examples thereof include compounds represented by the following general formula:

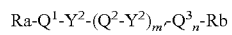

(where Ra and Rb are each a linear or branched alkyl group, alkoxy group, alkoxy carbonyl group, alkanoyloxy group, or alkoxy carbonyloxy group; $Q^1$, $Q^2$, and $Q^3$ are each a 1,4-phenylene group, a 1,4-cyclohexylene group, a pyridine-2,5-diyl group, a pyrazine-2,5-diyl group, a pyridazine-3,6-diyl group, or a 1,3-dioxane-2,5-diyl group, in which these groups may have a substituent group such as a halogen atom, a hydroxyl group, or a cyano group; $Y^1$ and $Y^2$ are each —COO—, —OCO—, —CH$_2$O—, —OCH$_2$—, —CH$_2$CH$_2$—, —C≡C—, or a single bond; and m' and n are 0 or 1). These host liquid crystals can be used solely or in a combination of two or more.

The chiral dopant to be added to the host liquid crystal is not particularly limited as long as it has large spontaneous polarization and the ability to induce an appropriate spiral pitch, and one generally known as a material to be added to a liquid crystal composition showing a SmC phase can be used. Particularly, a material that can induce large spontaneous polarization with the addition of a small amount thereof is preferably used Examples of such a chiral dopant include compounds represented by the following general formula:

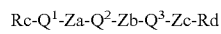

(where $Q^1$, $Q^2$, and $Q^3$ have the same meanings as those of the above general formula; Za and Zb are —COO—, —OCO—, —CH$_2$O—, —OCH$_2$—, —CH$_2$CH$_2$—, —C≡C—, —CH=N—, —N=N—, —N(→O)=N—, —C(=O)S—, or a single bond; Rc is a linear or branched alkyl group, alkoxy group, alkoxy carbonyl group, alkanoyloxy group, or alkoxy carbonyloxy group which may have an asymmetric carbon atom; Rd is a linear or branched alkyl group, alkoxy group, alkoxy carbonyl group, alkanoyloxy group, or alkoxy carbonyloxy group which has an asymmetric carbon atom; and Rc and Rd may be substituted with a halogen atom, a cyano group, or a hydroxyl group). These chiral dopants can be used solely or in combination of two or more of them.

One example of the ferroelectric liquid crystal of the second embodiment includes "FELIXM4851-100" manufactured by AZ Electronic Materials.

3. Other Compounds

In addition to the above-described liquid crystal compounds and ferroelectric liquid crystals, the ferroelectric liquid crystal composition of the present invention may further contain any optional compound. As such optional compound, one having a function that meets the intended use of the ferroelectric liquid crystal composition of the present invention can be used. An example of such a compound includes a phenylpyrimidine compound represented by the following general formula (*). When such a phenylpyrimidine compound is used, there is an advantage that the intensity of spontaneous polarization, viscosity, and spiral pitch of the ferroelectric liquid crystal can be controlled.

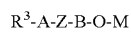 (*)

In the formula (*), A and B are 1,4-phenylene, 1,4-phenylene whose one or two carbon atoms on the benzene ring are substituted with nitrogen, or 1,4-cyclohexylene; Z is a single bond, —O—CO—, or —CO—O—, or when A or B is 1,4-cyclohexylene, Z is an oxygen atom; $R^3$ is a linear or branched alkyl group having 2 to 20 carbon atoms or alkene; and O-M is a structure containing 2,3-dihaloalkoxy (—O—$CH_2$—CHF—CHF—$CH_2$—$R^4$, wherein $R^4$ is a linear or branched alkyl group having 2 to 20 carbon atoms, alkene, or —OCO—$R^5$ (in which $R^5$ is a linear or branched alkyl group having 2 to 20 carbon atoms or alkene)).

Alternatively, a phenylpyrimidine compound represented by the following general formula (**) may be contained in the ferroelectric liquid crystal composition of the present invention. Also in a case where such a phenylpyrimidine compound is used, there is an advantage that the intensity of spontaneous polarization, viscosity, and spiral pitch of the terroelectric liquid crystal can be controlled.

$$R^6\text{-}A\text{-}(X)_a\text{—}B\text{—}(Y)_b\text{—}C\text{-}(Z)_c\text{-}D\text{-}R^7 \qquad (**)$$

In the formula (**), where a, b, and c are each independently 1 or 0; $R^6$ is a linear or branched alkyl group having 1 to 8 carbon atoms; and $R^7$ is a optically-active halogenated alkyl group having 1 to 10 carbon atoms or halogenated aralkyl group.

Further, the formula (**) satisfies the following conditions:

(1) when a, b, and c are 1, A is —O—, B is a single bond, C is —COO—, D is —COOCH$_2$— or —OCO—, X and Z are a 1,4-phenylene group, and Y is a 2,5-pyrimidine group;

(2) when a and b are 1, c is 0, and C is —OCO—, A is —O—, B and D are a single bond, and X and Y are a 1,4-phenylene group or a 2,5-pyrimidine group; and (3) when a and b are 1, c is 0, and C is —COO—, A is —O— or —COO—, B and D are a single bond, and X and Y are a 1,4-phenylene group or a 2,5-pyrimidine group.

4. Intended Use of Ferroelectric Liquid Crystal Composition

The intended use of the ferroelectric liquid crystal composition of the present invention is not particularly limited, but is mainly used for producing a liquid crystal device. Generally, a liquid crystal device has a structure in which a liquid crystal layer composed of a liquid crystal composition is interposed between two substrates each having an electrode and an alignment layer. The ferroelectric liquid crystal composition of the present invention is mainly used for forming such a liquid crystal layer. By using the ferroelectric liquid crystal composition of the present invention for that purpose, it is possible to obtain a liquid crystal device having excellent suitability for displaying moving images and excellent contrast characteristics.

It is to be noted that in a case where the liquid crystal layer is formed using the ferroelectric liquid crystal composition of the present invention, the ferroelectric liquid crystal composition of the present invention may be used solely or in combination with one or more other liquid crystal materials.

C. Ferroelectric Liquid Crystal Device

The ferroelectric liquid crystal device according to an embodiment of the present invention has a structure in which a first liquid crystal display substrate having a first substrate, a first electrode provided on the first substrate, and a first alignment layer provided on the first electrode and exerting alignment-regulating force on ferroelectric liquid crystal, and a second liquid crystal display substrate having a second substrate, a second electrode provided on the second substrate, and a second alignment layer provided on the second electrode and exerting alignment-regulating force on ferroelectric liquid crystal are arranged such that the first alignment layer and the second alignment layer are opposed to each other, and a liquid crystal layer containing ferroelectric liquid crystal is interposed between the first liquid crystal display substrate and the second liquid crystal display substrate. The ferroelectric liquid crystal device according to an embodiment of the present invention is characterized in that the liquid crystal layer contains the liquid crystal compound according to an embodiment of the present invention.

Such a ferroelectric liquid crystal device according to an embodiment of the present invention will be described with reference to the accompanying drawing FIG. 1 is a schematic view showing one example of a ferroelectric liquid crystal device according to an embodiment of the present invention. As shown in FIG. 1, a ferroelectric liquid crystal device 10 has a structure in which a first liquid crystal display substrate 1 having a first substrate 1a, a first electrode 1b provided on the first substrate 1a, and a first alignment layer 1c provided on the first electrode 1b and exerting alignment-regulating force on ferroelectric liquid crystal; a second liquid crystal display substrate 2 having a second substrate 2a, a second electrode 2b provided on the second substrate 2a, and a second alignment layer 2c provided on the second electrode 2b and exerting alignment-regulating force on ferroelectric liquid crystal are arranged such that the first alignment layer 1c and the second alignment layer 2c are opposed to each other; and a liquid crystal layer 3 containing ferroelectric liquid crystal is interposed between the first liquid crystal display substrate 1 and the second liquid crystal display substrate 2.

The ferroelectric liquid crystal device 10 according to an embodiment of the present invention shown by way of example is characterized in that the liquid crystal layer 3 contains the liquid crystal compound of the present invention.

By using the liquid crystal layer containing the liquid crystal compound of the present invention, it is possible to obtain a ferroelectric liquid crystal device having excellent contrast characteristics.

The ferroelectric liquid crystal device according to an embodiment of the present invention includes at least the first liquid crystal display substrate, the second liquid crystal display substrate, and the liquid crystal layer, but if necessary, may further include any other optional components.

Hereinafter, these components of the ferroelectric liquid crystal device according to an embodiment of the present invention will be described in order.

1. Liquid Crystal Layer

A liquid crystal layer to be used in the embodiment of the present invention contains a ferroelectric liquid crystal and the liquid crystal compound of the present invention. The ferroelectric liquid crystal device according to an embodiment of the present invention having such a liquid crystal layer containing the liquid crystal compound of the present invention can have excellent contrast characteristics.

Hereinafter, the liquid crystal layer will be described in detail.

(1) Liquid Crystal Compound

A liquid crystal compound to be used has a structure represented by the formula (I).

The liquid crystal layer to be used contains only one or two or more kinds of the liquid crystal compounds, but preferably contains two or more kinds of the liquid crystal compounds. This is because the use of two or more kinds of the liquid crystal compounds for producing a liquid crystal device may contribute to enhancement of other characteristics associated with the display quality of the liquid crystal device. For example, by using a mixture of the liquid crystal compounds different in the number of carbon atoms of each of the alkyl groups represented by $R^1$ and $R^2$ in the formula (I), it is possible to prevent the crystallization of the liquid crystal compounds over a wide range of temperatures, thereby enabling a ferroelectric liquid crystal device having a wide driving temperature margin to be obtained.

It is to be noted that the liquid crystal compound to be used according to an embodiment of the present invention is the same as the liquid crystal compound described in the paragraph "A. Liquid Crystal Compound", and therefore the description thereof will not be repeated here.

(2) Ferroelectric Liquid Crystal

Next, a ferroelectric liquid crystal to be used in an embodiment of the present invention will be described. A ferroelectric liquid crystal of the present invention is not particularly limited as long as it has compatibility to the liquid crystal compound to be used in any embodiment of the present invention and can exhibit a chiral smectic C (SmC*) phase.

It is noted that the ferroelectric liquid crystal to be used in any embodiment of in the present invention is the same as the ferroelectric liquid crystal described in the paragraph "B. Ferroelectric Liquid Crystal Composition", and therefore the detailed description thereof will not be repeated here.

The liquid crystal layer to be used in an embodiment of the present invention contains only one kind or two or more kinds of the ferroelectric liquid crystals, but preferably contains two or more kinds of the ferroelectric liquid crystals. By using two or more kinds of the ferroelectric liquid crystals, it is possible to obtain a ferroelectric liquid crystal device of the present invention having a wide driving temperature margin.

(3) Other Compounds

In addition to the above-described liquid crystal compound and ferroelectric liquid crystal, the liquid crystal layer to be used in an embodiment of the present invention may further contain any optional compound. As such a compound, any compound having a desired function that meets display quality required of the ferroelectric liquid crystal device according to an embodiment of the present invention can be used.

It is to be noted that specific examples of such a compound are the same as those described in the paragraph "B. Ferroelectric Liquid Crystal Composition", and therefore the description thereof will not be repeated here.

(4) Liquid Crystal Layer

The liquid crystal layer to be used in an embodiment of the present invention is characterized by containing the liquid crystal compound described above. The amount of the liquid crystal compound contained in the liquid crystal layer is not particularly limited as long as it is enough to allow the ferroelectric liquid crystal device according to an embodiment of the present invention to have a desired level of contrast, and can be appropriately determined according to such as the kind of ferroelectric liquid crystal to be used together with the liquid crystal compound. The amount of the liquid crystal compound contained in the liquid crystal layer to be used in an embodiment of the present invention is preferably in the range of 3 to 40% by mass, particularly preferably in the range of 5 to 30% by mass. If the amount of the liquid crystal compound contained in the liquid crystal layer is less than the above range, there may be a case where it is difficult to adjust the contrast of the ferroelectric liquid crystal device of the present invention to a desired level. On the other hand, if the amount of the liquid crystal compound contained in the liquid crystal layer exceeds the above range, there may be a risk that the orientation of the ferroelectric liquid crystal in the liquid crystal layer is hindered.

The thickness of the liquid crystal layer to be used in an embodiment of the present invention is preferably in the range of 1.2 to 3.0 µm, more preferably in the range of 1.3 to 2.5 µm, and even more preferably in the range of 1.4 to 2.0 µm. If the thickness of the liquid crystal layer is too small, there is the risk that the contrast of the ferroelectric liquid crystal device of the present invention is lowered. On the other hand, if the thickness of the liquid crystal layer is too large, there is the possibility that the ferroelectric liquid crystal is not easily aligned.

2. First and Second Liquid Crystal Display Substrates

Next, a first liquid crystal display substrate and a second liquid crystal display substrate to be used in an embodiment of the present invention will be described. A first liquid crystal display substrate to be used in an embodiment of the present invention has a first substrate, a first electrode provided on the first substrate, and a first alignment layer provided on the first electrode and exerting alignment-regulating force on ferroelectric liquid crystal.

A second liquid crystal display substrate to be used in an embodiment of the present invention has a second substrate, a second electrode provided on the second substrate, and a second alignment layer provided on the second electrode and exerting alignment-regulating force on ferroelectric liquid crystal.

Hereinafter, such first and second liquid crystal display substrates will be described in detail.

(1) First and Second Substrates

The first and second substrates to be used according to an embodiment of the present invention preferably have a transmission in the visible light region of 80% or higher, and more preferably 90% or higher. By setting the transmission of the first and second substrates to a value within the above range, it is possible to prevent, for example, the lowering of display luminance of the ferroelectric liquid crystal device according to an embodiment of the present invention.

In this regard, it is noted that the transmission of a transparent substrate can be measured in accordance with JIS K7361-1 (Determination of the total light transmittance of plastic-transparent materials).

As the first and second substrates to be used according to an embodiment of the present invention, substrates generally used for producing liquid crystal displays, such as glass substrates and resin film substrates can be used without particular limitation. Examples of such resin film substrates include: thermoplastic plastic films such as polyethylene terephthalate (PET) films, polycarbonate (PC) films, and polyethersulfone (PES) films; and films made of cross-linkable resins such as epoxy resins, organic-inorganic composite materials, polyimide (PI), polyamide, aromatic polyamide, polyethylene (PE), polypropylene (PP), polyester, polyolefin, polyacrylonitrile, ethylene-vinylacetate (EVA) copolymers, triacetyl cellulose (TAC), polyethylene naphthalate, polyphenylene sulfide (PPS), and polyether ether ketone (PEEK).

Each of the first and second substrates to be used in the present invention has a single layer structure or a multilayered laminate structure. The multilayered laminate structure is composed of plural layers having the same composition or different compositions.

Usually, the thicknesses of the first and second substrates to be used in an embodiment of the present invention are preferably in the range of 0.05 to 3 µm, and particularly preferably in the range of 0.2 to 2 µm. It is to be noted that when the first and second substrates have a multilayered laminate structure, the thickness of each substrate refers to the total thickness of all the layers constituting the substrate.

Further, the first and second substrates to be used in an embodiment of the present invention have a surface roughness (RSM value) of preferably 10 nm or less, more preferably 3 nm or less, and particularly preferably 1 nm or less.

In this regard, it is to be noted that the surface roughness of the substrate can be measured with an atomic force microscope (AFM).

It is to be noted that the first and second substrates to be used in an embodiment of the present invention may be the same substrate or different from each other. In an embodiment of the present invention, the first and second substrates are considered as different substrates not only when the first and second substrates are made of different materials but also when the first and second substrates are different in such as thickness or surface morphology.

(2) First and Second Electrodes

The first and second electrodes to be used in an embodiment of the present invention are formed on the first and second substrates, respectively, and have the function of driving the ferroelectric liquid crystal of the ferroelectric liquid crystal device of the present invention.

The first and second electrodes to be used in the present invention are not particularly limited as long as they have the function of driving the ferroelectric liquid crystal of the terroelectric liquid crystal device according to an embodiment of the present invention. As such first and second electrodes, electrodes generally used as common electrodes for liquid crystal displays can be used without particular limitation. Among them, electrodes made of indium oxide, tin oxide, or indium tin oxide (ITO) are preferably used as the first and second electrodes in an embodiment of the present invention.

It is noted that the first and second electrodes to be used in the present invention may be the same electrode or different from each other. In an embodiment of the present invention, the first and second electrodes are considered as different electrodes not only when the first and second electrodes are made of different materials but also when the first and second electrodes are different in such as thickness or surface morphology.

(3) First and Second Alignment Layers

The first and second alignment layers to be used in the present invention are not particularly limited as long as they can exert alignment-regulating force on ferroelectric liquid crystal. Examples of such first and second alignment layers include alignment layers such as rubbing layers obtained by subjecting polymeric materials, such as polyimide, to rubbing treatment and photo alignment layers obtained by subjecting photo alignment materials to alignment treatment. Among these alignment layers, photo alignment layers as the alignment treatment layer are preferably used as the first and second alignment layers in the present invention. This is because a photo alignment layer can be obtained by non-contact alignment treatment and therefore static electricity or dust is not generated, and the alignment treatment can be quantitatively controlled.

A photo alignment material constituting the photo alignment layer is not particularly limited as long as it has the effect of generating photo-excited reaction to align ferroelectric liquid crystal (photoaligning) when irradiated with light. In an embodiment of the present invention, the wavelength range of light that causes photo-excited reaction in the photo alignment material is preferably in the range of 10 to 400 nm, and particularly preferably in the range of 250 to 380 nm.

Such a photo alignment material can be classified into a photoreactive type material that generates photoreaction to give anisotropy to a photo alignment layer, and a photo-isomerization type material which generates photo-isomerization reaction to give anisotropy to a photo alignment layer. Examples of such photoreactive type material and photo-isomerization type material to be used in the present invention include materials described in, for example, Japanese Patent Application Laid-Open (JP-A) No. 2006-323223.

Each of the first and second alignment layers to be used in an embodiment of the present invention may be formed by fixing a reactive curable liquid crystal as a reactive curable liquid crystal layer on the alignment treatment layer. By using alignment layers having such a reactive curable liquid crystal layer thereon as the first and second alignment layers, it is possible to improve alignment stability of the ferroelectric liquid crystal of the ferroelectric liquid crystal device according to an embodiment of the present invention.

The reason why the alignment stability of the ferroelectric liquid crystal can be improved by using alignment layers having the reactive curable liquid crystal layer thereon as the first and second alignment layers is as follows.

As described above, since the reactive curable liquid crystal layer is formed by fixing a reactive curable liquid crystal on the alignment treatment layer, the reactive curable liquid crystal contained in the reactive curable liquid crystal layer is fixed with it being aligned due to the function of the alignment treatment layer. Therefore, the reactive curable liquid crystal layer can function as an alignment layer for aligning the ferroelectric liquid crystal.

Further, since the reactive curable liquid crystal is fixed, it is insensitive to such as temperature. Therefore, an alignment layer having the reactive curable liquid crystal layer thereon has higher temporal stability for alignment-regulating force as compared to when the alignment layer is singly used.

Furthermore, since the reactive curable liquid crystal has a structure relatively similar to that of the ferroelectric liquid crystal, the reactive curable liquid crystal strongly interacts with the ferroelectric liquid crystal. Therefore, an alignment layer having the reactive curable liquid crystal layer thereon can control the alignment of the ferroelectric liquid crystal more effectively as compared to a case where the alignment treatment layer is singly used.

For these reasons, by using the first and second alignment layers having the reactive curable liquid crystal layer thereon, it is possible to improve the alignment stability of the ferroelectric liquid crystal.

The reactive curable liquid crystal to be used for forming the reactive curable liquid crystal layer is not particularly limited as long as it is regularly oriented due to the function of the alignment treatment layer. Particularly, according to an embodiment of the present invention, a reactive curable liquid crystal showing a nematic phase is preferably used because, among various liquid crystal phases, alignment of a nematic phase is relatively easily controlled.

Further, the reactive curable liquid crystal to be used in an embodiment of the present invention preferably contains a polymerizable liquid crystal material. By using schwa reactive curable liquid crystal, it is possible to fix the alignment state of the reactive curable liquid crystal.

As such a polymerizable liquid crystal material, any one of a polymerizable liquid crystal monomer, a polymerizable liquid crystal oligomer, and a polymerizable liquid crystal polymer can be used, but in the present invention, a polymerizable liquid crystal monomer is preferably used. This is because as compared to other polymerizable liquid crystal materials, that is, a polymerizable liquid crystal oligomer and a polymerizable liquid crystal polymer, a polymerizable liquid crystal monomer can be aligned at a lower temperature, and it has high alignment sensitivity and is therefore easily aligned. The polymerizable liquid crystal monomer to be used in an embodiment of the present invention is not particularly limited as long as it is a liquid crystal monomer having a polymerizable functional group. Examples of such a polymerizable liquid crystal monomer include a monoacrylate monomer and a diacrylate monomer. Examples of the monoacrylate monomer and the diacrylate monomer to be used in an embodiment of the present invention include those described in, for example, JP-A No. 2006-323223.

Furthermore, according to an embodiment of the present invention, as needed, a photo polymerization initiating agent or a polymerization inhibiting agent may be added to the reactive curable liquid crystal. For example, at the time of polymerizing a polymerizable liquid crystal material by the electron beam irradiation, a photo polymerization initiating agent may not be needed, however, in the case of a polymerization commonly conducted by such as, the ultraviolet ray exposure a photo polymerization initiating agent is generally used for promoting the polymerization.

As examples of photo polymerization initiating agents to be used in an embodiment of the present invention, benzyl (it is also referred to as bibenzoyl), benzoin isobutyl ether, benzoin isopropyl ether, benzophenone, benzoyl benzoic acid, methyl benzoyl benzoate, 4-benzoyl-4'-methyl diphenyl sulfide, benzyl methyl ketal, dimethyl amino methyl benzoate, 2-n-butoxy ethyl-4-dimethyl amino benzoate, p-dimethyl amino isoamyl benzoate, 3,3'-dimethyl-4-methoxy benzophenone, methylobenzoyl formate, 2-methyl-1-(4-(methyl thio) phenyl)-2-morpholino propane-1-on, 2-benzyl-2-dimethyl amino-1-(4-morpholino phenyl)-butane-1-on, 1-(4-dodecyl phenyl)-2-hydroxy-2-methyl propane-1-on, 1-hydroxy cyclohexyl phenyl ketone, 2-hydroxy-2-methyl-1-phenyl propane-1-on, 1-(4-isopropyl phenyl)-2-hydroxy-2-methyl propane-1-on, 2-chloro thioxantone, 2,4-diethyl thioxantone, 2,4-diisopropyl thioxantone, 2,4-dimethyl thioxantone, isopropyl thioxantone, or 1-chloro-4-propoxy thioxantone can be presented. In addition to the photo polymerization initiating agent, a sensitizing agent may be added within a range of not deteriorating the object of the present invention.

When the photo polymerization initiating agent is used, a photo polymerization initiating auxiliary agent may be used together with the photo polymerization initiating agent. Examples of such a photo polymerization initiating auxiliary agent include, but are not limited to, tertiary amines such as triethanolamine and methyl diethanol amine and benzoic acid derivatives such as 2-dimethylaminoethylbenzoic acid, 4-dimethylaminoethyl benzoate.

It is noted that the first alignment layer and the second alignment layer may be the same alignment layer or different from each other. In an embodiment of the present invention, the first and second alignment layers are considered as different alignment layers not only when the first and second alignment layers are made of different materials or have different structures but also when they are different in such qualities as thickness or surface morphology. In an embodiment of the present invention, it is preferred that each of the first and second alignment layers has the alignment treatment layer and a reactive curable liquid crystal layer formed thereon and the composition of a reactive curable liquid crystal constituting the reactive curable liquid crystal layer is different between the first and second alignment layers By using such first and second alignment layers, it is possible to inhibit the generation of alignment defects such as zigzag defects, hairpin defects, or double domains in the ferroelectric liquid crystal device of the present invention, thereby realizing a monostable operation mode.

(4) Other Components

The first and second liquid crystal display substrates to be used in an embodiment of the present invention may further include any component in addition to the above-described components. Such a component to be used in an embodiment of the present invention is not particularly limited, and therefore any component having a desired function that meets the intended use of the ferroelectric liquid crystal device of the present invention can be used. Examples of such a component include a color filter layer having a plurality of colored layers and a TFT electrode layer having a plurality of TFT electrodes In the case where such color filter layer and TFT electrode layer are used, they are formed on at least one of the first and second liquid crystal display substrates.

It is to be noted that the color filter layer and the TFT electrode layer described above are similar to those generally used for producing liquid crystal devices, and therefore the description thereof will not be repeated here.

3. Ferroelectric Liquid Crystal Device

The ferroelectric liquid crystal device according to an embodiment of the present invention is preferably driven by an active matrix system, and can be used as a color liquid crystal device by adopting a color filter system or a field sequential color system.

The ferroelectric liquid crystal device of the present invention may have a color filter layer disposed on one of the first and second liquid crystal display substrates so as to be used as a color display. However, by adopting a field sequential color system utilizing a high speed response property of ferroelectric liquid crystal and an LED light source, the ferroelectric liquid crystal device according to an embodiment of the present invention can be used as a color display without using a micro color filter layer.

In the case where the ferroelectric liquid crystal shows mono-stability, the ferroelectric liquid crystal device of the present invention is basically driven by an active matrix system using a TFT, but can also be driven by a segment system.

4. Method of Producing Liquid Crystal Device

Next, a method of producing a ferroelectric liquid crystal device according to an embodiment of the present invention will be described. The ferroelectric liquid crystal device according to an embodiment of the present invention can be produced by a generally well known method of producing a liquid crystal device, except that a ferroelectric liquid crystal composition constituting a liquid crystal layer contains the liquid crystal compound according to an embodiment of the present invention. An example of such a production method includes a method comprising a step of filling liquid crystal by dropping a ferroelectric liquid crystal composition containing the liquid crystal compound described above onto the first alignment layer of the first liquid crystal display substrate; a step of sticking the first liquid crystal display substrate, in which the ferroelectric liquid crystal composition has been filled, and the second liquid crystal display substrate together under vacuum such that the first alignment layer and the second alignment layer are opposed to each other; and a step of orienting a ferroelectric liquid crystal contained in the ferroelectric liquid crystal composition.

Hereinafter, this production method will be described as one example of a method of producing a ferroelectric liquid crystal device according to an embodiment of the present invention.

(1) Step of Filling Liquid Crystal

First of all, the step of filling a liquid crystal will be described. In this step, a ferroelectric liquid crystal composition containing the above-described liquid crystal compound is dropped onto the first alignment layer of the first liquid crystal display substrate to fill the ferroelectric liquid crystal composition in the first liquid crystal display substrate.

A method of dropping the ferroelectric liquid crystal composition to be employed in this step is not particularly limited as long as a predetermined amount of a ferroelectric liquid crystal can be dropped into each space between spacers. Examples of such a method include methods generally used for dropping a liquid crystal by an ODF system, such as an ink-jet method using an ink-jet head for dropping a ferroelectric liquid crystal and a dispenser method using a dispenser for dropping a ferroelectric liquid crystal.

It is to be noted that the ferroelectric liquid crystal composition to be used in this step contains the liquid crystal compound according to the present invention Examples of such a ferroelectric liquid crystal composition include those described in the paragraph "B. Ferroelectric Liquid Crystal Composition"

(2) Step of Sticking Substrates

Next, the step of sticking substrates will be described. In this step, the first liquid crystal display substrate, in which the ferroelectric liquid crystal composition has been filled in the liquid crystal filling step, and the second liquid crystal display substrate are stuck together under a vacuum such that the first alignment layer and the second alignment layer are opposed to each other.

A method of sticking the first and second liquid crystal display substrates to be employed in this step is not particularly limited as long as they can be stuck together under a predetermined vacuum condition. Examples of such a method include well known methods generally used for sticking substrates together in producing a liquid crystal device.

(3) Step of Orienting Liquid Crystal

In the step of orienting a liquid crystal, a ferroelectric liquid crystal contained in the ferroelectric liquid crystal composition encapsulated between the first and second liquid crystal display substrates stuck together in the substrate sticking step is oriented. More specifically, it can be said that this step is carried out to put the ferroelectric liquid crystal in a chiral smectic C phase state because the ferroelectric liquid crystal performs switching function in the liquid crystal device when it is in a chiral smectic C phase state.

A method of orienting the ferroelectric liquid crystal to be employed in this step is not particularly limited as long as the ferroelectric liquid crystal can be put in a chiral smectic C phase state. As such a method, there is generally used a method in which the ferroelectric liquid crystal is heated to a transition temperature from a chiral smectic C phase to a nematic phase or isotropic phase or higher, and then the filled ferroelectric liquid crystal is cooled to obtain a chiral smectic C phase.

It is noted that the present invention is not limited to the above embodiments. These embodiments are examples, and all modifications having substantially the same structure and producing the same effects and advantages as the technical concept recited in the claims of the present invention are included in the technical scope of the invention.

EXAMPLES

Hereinafter, the present invention will be described in more detail with reference to the following examples.

1. Example 1

(1) Synthesis of Liquid Crystal Compound

A liquid crystal compound I was obtained by the following synthesis method.

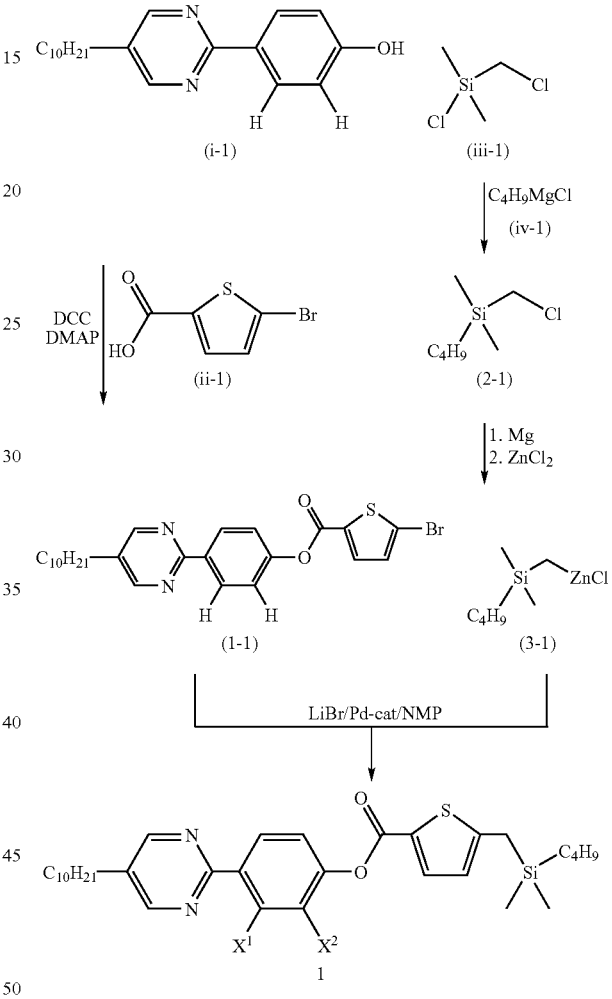

As a first process, a mixture of pyrimidlylphenol compound (i-1) (3.7 g), thiophenecarboxylic acid compound (ii-1) (2.5 g), DCC (2.6 g) and DMAP (20 mg) in 100 ml of dry methylene chloride was stirred at room temperature over night. Then the white solid was filtered and filtrate was concentrated. The residue was further purified by flash chromatography to give pure compound (1-1) (ca. 80% yielded).

As a second process, a compound (iii-1) (7.0 g, 49 mmol) and 30 ml THF (anhydrous), and the mixture cooled in an ice bath. A compound (iv-1) (2.0 m in THF) (49 mmol) was added dropwise with stirring over 15 minutes. The mixture was stirred at low temperature for 1 hour, followed by 1 hour at room temperature. 50 mL saturated $NH_4Cl$ solution was added and the mixture was extracted with 3×50 mL hexane, organic extract was dried ($MgSO_4$) and filtered. Removal of solvent from filtrate gave a colorless liquid compound (2-1)

was obtained by distillation under reduced pressure. The compound (2-1) was distilled at 28° C. (bath temperature 50° C.) and yielded 6.3 g.

As a third process, a flame dried flask was charged with Mg (0.35 g, 14.4 mmol), 20 mL THF, the compound (2-1) (2.0 g, 12.1 mmol) and a crystal of iodine. The mixture was sonicated for 5 hours. To the resulting brown solution, a solution of $ZnCl_2$/THF (0.5M) (25 mL, 12.5 mmol) was added. The mixture was stirred overnight (16 hours) and a solution containing a compound (3-1) was obtained.

As fourth process, the resulting supernatant solution prepared in the third process (20 mL) was added to a mixture of compound (1-1) (1.5 g), LiBr (1.0 g) and Pd catalyst in 20 mL NMP, and the reaction mixture was stirred for 4 hours at room temperature. Water (20 mL) was added, extracted with 3×25 mL ethyl acetate, the organic extract was washed with water, dried (MgSO4), filtered over celite and solvent was removed under reduced pressure to give a yellow liquid residue The crude product was loaded onto a silica gel column, and eluted with hexane/ethylacetate (90/10). Removal of solvent from middle fraction gave the product as a pale semi-solid, 0.85 g. Crystallization from hexane at −20° C. gave the product as white solid, which was filtered, washed with cold hexane, dried to obtain a liquid crystal compound 1 and yield 0.3 g.

(2) Preparation of Ferroelectric Liquid Crystal Composition

The liquid crystal compound 1 synthesized by the above method was mixed with other liquid crystal compounds 2 to 7 at a ratio shown in the following Table 1 to obtain a terroelectric liquid crystal composition A exhibiting a phase series of SmC*-N-I.

TABLE 1

| | | Unit: % by mass | | |
|---|---|---|---|---|
| | | Ferroelectric Liquid Crystal Composition A | Ferroelectric Liquid Crystal Composition B | Ferroelectric Liquid Crystal Composition C |
| 1 | $C_9H_{19}$—[pyrimidine]—[phenyl]—O—C(O)—[thiophene]—$CH_2$—Si(Me)$_2$—$C_4H_9$ | 15.0 | 30.0 | 0.0 |
| 2 | $C_8H_{17}$—[pyrimidine]—[phenyl]—O—C(O)—[cyclohexyl]—$C_4H_9$ | 4.3 | 3.5 | 5.0 |
| 3 | $C_8H_{17}$—[pyrimidine]—[phenyl]—$OC_6H_{13}$ | 16.2 | 13.3 | 19.0 |
| 4 | $C_8H_{17}O$—[pyrimidine]—[phenyl]—$OC_8H_{17}$ | 16.2 | 13.3 | 19.0 |
| 5 | $C_{11}H_{23}O$—[pyrimidine]—[phenyl]—$OC_8H_{17}$ | 16.2 | 13.3 | 19.0 |
| 6 | $C_8H_{17}$—[pyrimidine]—[phenyl]—$OC_{12}H_{25}$ | 16.2 | 13.3 | 19.0 |
| 7 | $C_8H_{17}$—[pyrimidine]—[difluorophenyl]—O—$CH_2$—CHF—$C_5H_{11}$ (with F) | 16.2 | 13.3 | 19.0 |

(3) Production of Liquid Crystal Device

A glass substrate having an ITO electrode formed thereon was thoroughly washed, spin-coated with a transparent resist (manufactured by JSR Corporation under the trade name of "NN780"), dried under a reduced pressure, and pre-baked at 90° C. for 3 minutes. The pre-baked resist was exposed to ultraviolet rays at 100 mJ/cm² through a mask, developed using an inorganic alkali solution, and post-baked at 230° C. for 30 minutes to form columnar spacers having a height of 1.5 μm.

Next, the substrate having the spacers formed thereon was spin-coated with a 2% by mass solution of a photo-dimerization reactive material (manufactured by Rolic Technologies Ltd. under the trade name of "ROP-102") for forming a photo alignment layer dissolved in cyclopentanone, dried at 130° C. for 10 minutes, and exposed to linearly-polarized ultraviolet rays at about 100 mJ/cm² to carry out alignment treatment.

On the other hand, a substrate having an ITO electrode formed thereon was spin-coated with a 2% by mass solution of a photo-dimerization reactive material (manufactured by Rolic Technologies Ltd. under the trade name of "ROP-102") for forming a photo alignment layer dissolved in cyclopentanone, dried at 130° C. for 10 minutes, and exposed to linearly-polarized ultraviolet rays at about 100 mJ/cm² to carry out alignment treatment. Further, the substrate having a photo alignment layer was spin-coated with a 5% by mass solution of polymerizable liquid crystal (manufactured by Rolic Technologies Ltd. under the trade name of "ROF-5101") dissolved in cyclopentanone, dried at 80° C. for 3 minutes, and exposed to ultraviolet rays at about 1000 mJ/cm² to carry out treatment.

The ferroelectric liquid crystal composition A was attached to the upper part of an injection port, and injection was carried out using an oven at a temperature higher by 10 to 20° C. than a phase transition temperature between nematic and isotropic phases, and the temperature was slowly returned to room temperature.

2. Example 2

A liquid crystal device was produced in the same manner as in Example 1 except that the ferroelectric liquid crystal composition A was replaced with a terroelectric liquid crystal composition B obtained by mixing liquid crystal compounds at a ratio shown in Table 1.

3. Comparative Example

A liquid crystal device was produced in the same manner as in Example 1 except that the ferroelectric liquid crystal composition A was replaced with a ferroelectric liquid crystal composition C obtained by mixing liquid crystal compounds at a ratio shown in Table 1.

4. Evaluation

Figure 2:
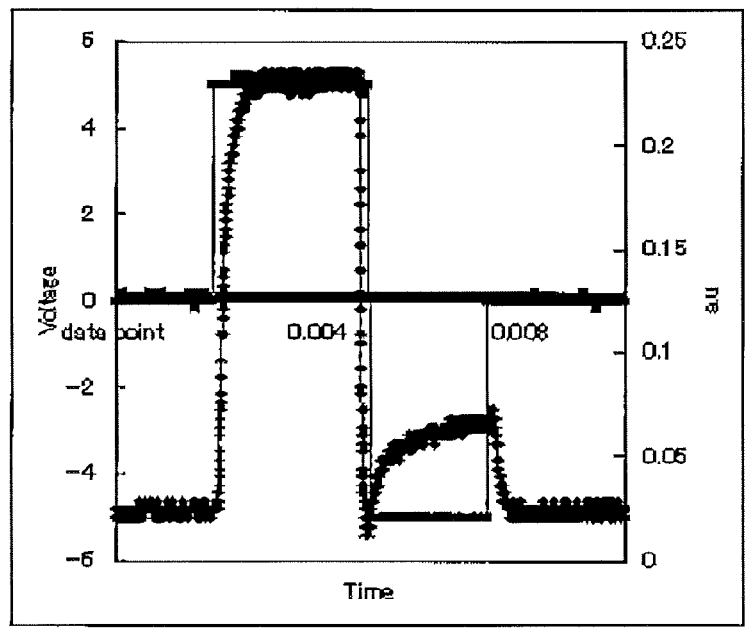
FIG. 2 is a graph showing one example of a pattern of voltage applied to a liquid crystal device.
Figure 3:
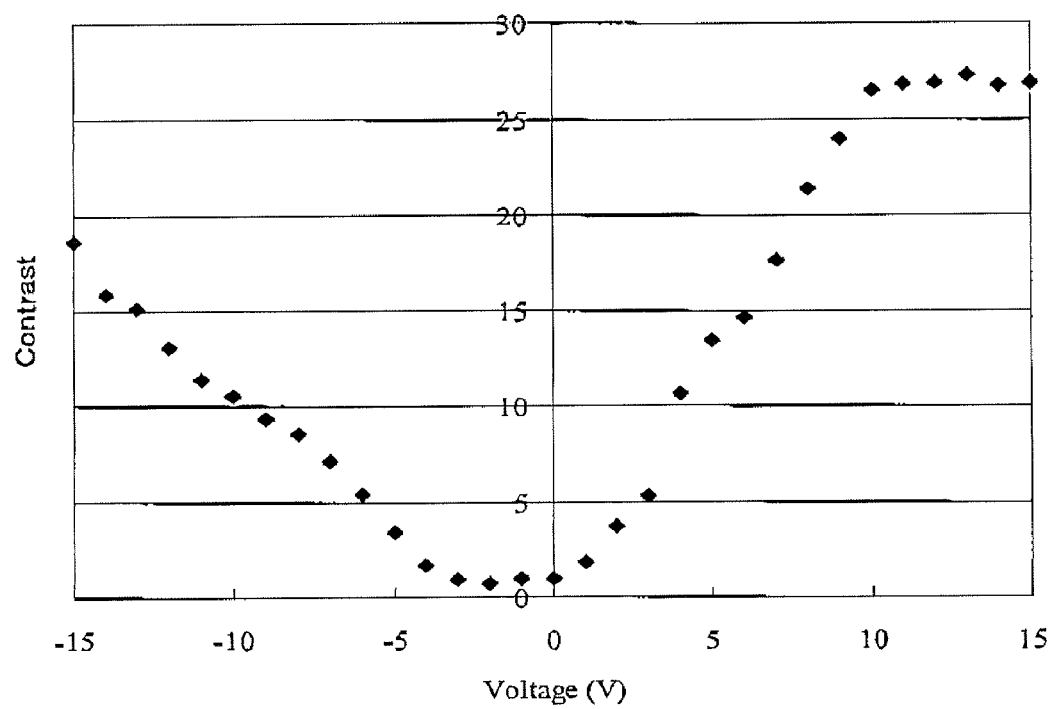
FIG. 3 is a graph showing one example of a relationship between voltage applied to a liquid crystal device and the contrast of the liquid crystal device.
Figure 4:
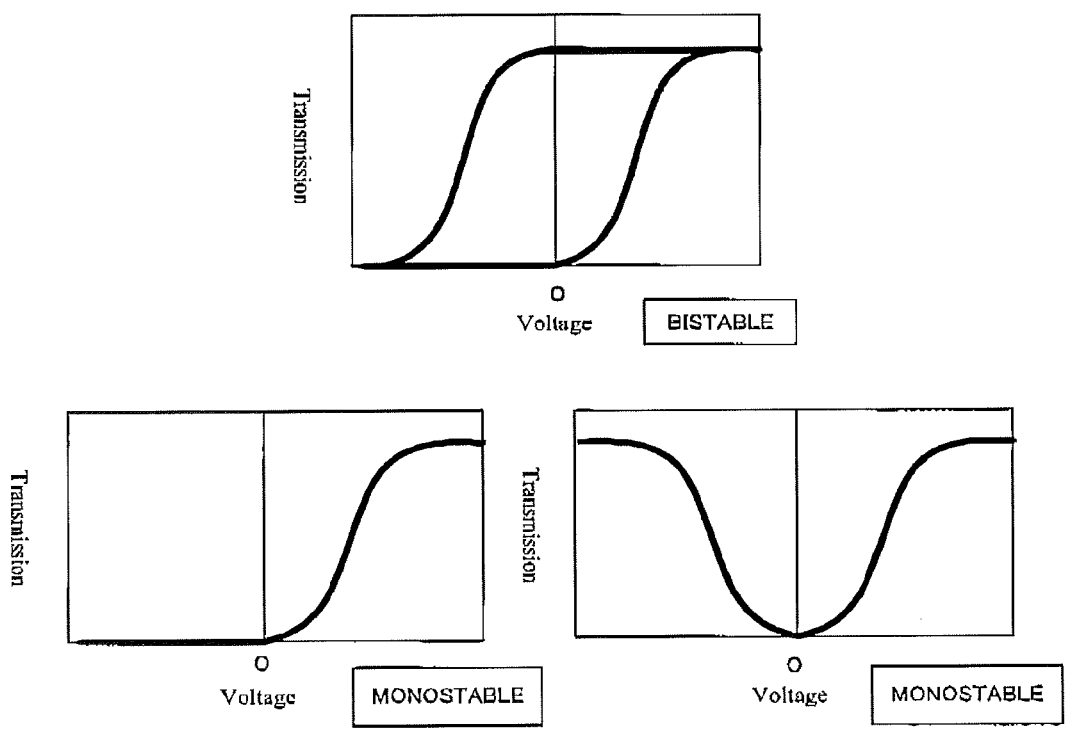
FIG. 4 is a graph showing changes in transmission as a function of voltage applied to ferroelectric liquid crystals.
Figure 5:
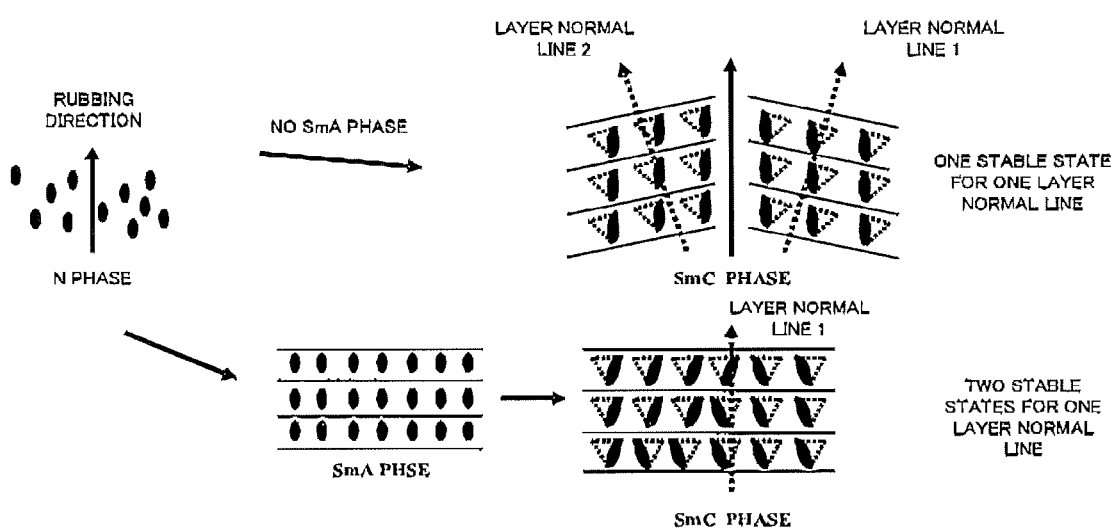
FIG. 5 is an illustration showing a difference of alignment defects based on a difference of phase series that ferroelectric liquid crystal has.

A rectangular wave having a frequency of 0.1 Hz and a voltage of 5 V shown in FIG. 2 was applied to the liquid crystal devices of the Examples and the Comparative Example to determine a relationship between transmitted light intensity and time. As a result, the amount of transmitted light was varied depending on whether the applied voltage was positive or negative. Then, the amount of transmitted light at the time only when a voltage, at which a large amount of transmitted light was achieved, was applied was integrated and compared to a case where no voltage was applied. In this way, the contrast of each of the liquid crystal devices was evaluated. FIG. 3 shows a relationship between voltage applied to the liquid crystal device of the Comparative Example and the contrast of the liquid crystal device of the Comparative Example.

The contrast of each of the liquid crystal devices of Examples 1 and 2 and the Comparative Example was determined when a voltage of 5 V was applied thereto, and as a result the contrast of the liquid crystal device of Example 1 was 39, the contrast of the liquid crystal device of Example 2 was 87, and the contrast of the liquid crystal device of Comparative Example was 13.4. From the result, it was found that the addition of the liquid crystal compound of the present invention significantly enhanced contrast. It will be clear that the present invention is well adapted to attain the ends and advantages mentioned as well as those inherent therein. While a various embodiments including the presently preferred one has been described for purposes of this disclosure, various changes and modifications may be made, which are well within the scope of the present invention. Numerous other changes may be made which will readily suggest themselves to those skilled in the art and which are encompassed in the spirit of the invention disclosed and as defined in the appended claims.

What is claimed is:

1. A liquid crystal compound having a structure represented by the following formula (I):

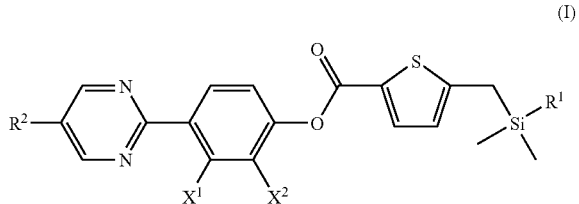

wherein $R^1$ is an alkyl group having 4 to 6 carbon atoms, $R^2$ is an alkyl group having 6 to 18 carbon atoms or an alkoxy group having 6 to 18 carbon atoms, and $X^1$ and $X^2$ are each independently hydrogen or fluorine.

2. The liquid crystal compound according to claim 1, wherein the liquid crystal compound having the formula (I) acts as a contrast enhancer enhancing a contrast of a ferroelectric liquid crystal device using a ferroelectric liquid crystal.

3. A ferroelectric liquid crystal composition comprising:
a liquid crystal compound having a structure represented by the following formula (I):

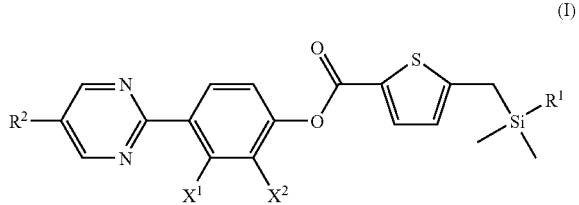

wherein $R^1$ is an alkyl group having 4 to 6 carbon atoms, $R^2$ is an alkyl group having 6 to 18 carbon atoms or an alkoxy group having 6 to 18 carbon atoms, and $X^1$ and $X^2$ are each independently hydrogen or fluorine; and
a ferroelectric liquid crystal.

4. A ferroelectric liquid crystal device comprising:
a first liquid crystal display substrate comprising:
  a first substrate;
  a first electrode formed on the first substrate; and
  a first alignment layer formed on the first electrode and exerting alignment-regulating force on a ferroelectric liquid crystal;

a second liquid crystal display substrate comprising:
  a second substrate;
  a second electrode formed on the second substrate; and
  a second alignment layer formed on the second electrode and exerting alignment-regulating force on a ferroelectric liquid crystal; and
a liquid crystal layer containing a ferroelectric liquid crystal, interposed between the first liquid crystal display substrate and the second liquid crystal display substrate which are arranged such that the first alignment layer and the second alignment layer are opposed to each other,
wherein the liquid crystal layer contains the liquid crystal compound having a structure represented by the following formula (I):

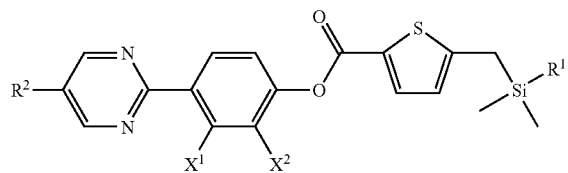

wherein $R^1$ is an alkyl group having 4 to 6 carbon atoms, $R^2$ is an alkyl group having 6 to 18 carbon atoms or an alkoxy group having 6 to 18 carbon atoms, and $X^1$ and $X^2$ are each independently hydrogen or fluorine.

* * * * *